United States Patent
Zhao et al.

(10) Patent No.: US 11,944,048 B2
(45) Date of Patent: Apr. 2, 2024

(54) DECISION-MAKING METHOD FOR VARIABLE RATE IRRIGATION MANAGEMENT

(71) Applicant: China Institute of Water Resources and Hydropower Research, Beijing (CN)

(72) Inventors: Weixia Zhao, Beijing (CN); Jiusheng Li, Beijing (CN); Yanfeng Li, Beijing (CN); Zhen Wang, Beijing (CN); Jun Wang, Beijing (CN)

(73) Assignee: CHINA INSTITUTE OF WATER RESOURCES AND HYDROPOWER RESEARCH, Beijing (CN)

( * ) Notice: Subject to any disclaimer, the term of this patent is extended or adjusted under 35 U.S.C. 154(b) by 357 days.

(21) Appl. No.: 17/343,748

(22) Filed: Jun. 10, 2021

(65) Prior Publication Data

US 2022/0279741 A1  Sep. 8, 2022

(30) Foreign Application Priority Data

Mar. 5, 2021 (CN) .......................... 202110243593.4

(51) Int. Cl.
*A01G 25/16* (2006.01)
*G01K 1/02* (2021.01)
*G01N 33/24* (2006.01)

(52) U.S. Cl.
CPC ......... *A01G 25/167* (2013.01); *A01G 25/162* (2013.01); *A01G 25/165* (2013.01); *G01K 1/026* (2013.01); *G01N 33/246* (2013.01); *G01N 2033/245* (2013.01)

(58) Field of Classification Search
CPC .... A01G 25/16; A01G 25/162; A01G 25/165; A01G 25/167
USPC ......................................................... 47/48.5
See application file for complete search history.

(56) References Cited

U.S. PATENT DOCUMENTS

| | | | |
|---|---|---|---|
| 8,401,705 B2 * | 3/2013 | Alexanian | A01G 25/16 239/69 |
| 8,793,024 B1 * | 7/2014 | Woytowitz | A01G 25/167 239/723 |
| 8,862,277 B1 * | 10/2014 | Campbell | A01G 25/167 700/284 |

(Continued)

*Primary Examiner* — David J Parsley
(74) *Attorney, Agent, or Firm* — Bayramoglu Law Offices LLC

(57) ABSTRACT

A decision-making method for variable rate irrigation management includes the following steps: S1: sampling a soil from a root zone of a crop in an area controlled by an irrigation sprinkler, and measuring compositions of separates of the sampled soil; S2: managing and dividing the area controlled by the irrigation sprinkler according to an AWC of the soil in the root zone of the crop; S3: constructing an optimized soil moisture sensor network; S4: placing ground-fixed canopy temperature sensors; S5: constructing an optimized airborne canopy temperature sensor network centered on the center pivot; and S6: performing a variable rate irrigation by using the optimized soil moisture sensor network, the fixed canopy temperature sensors, the optimized airborne canopy temperature sensor network and an automatic weather station. The method optimizes the placement and quantity of the soil moisture sensor network and the canopy temperature sensor network to improve the measurement accuracy.

9 Claims, 1 Drawing Sheet

(56) References Cited

U.S. PATENT DOCUMENTS

| | | | | |
|---|---|---|---|---|
| 9,200,985 B2* | 12/2015 | Rice | ............... | G01M 99/008 |
| 9,943,046 B2* | 4/2018 | Bermudez Rodriguez | ............... | |
| | | | | A01G 25/092 |
| 10,192,185 B2* | 1/2019 | Tomii | ............... | G06Q 50/02 |
| 10,602,682 B1* | 3/2020 | Wardle | ............... | G05B 19/042 |
| 10,973,182 B1* | 4/2021 | Bangerter | ............... | A01G 25/167 |
| 11,707,026 B1* | 7/2023 | Hansen | ............... | A01G 25/167 |
| | | | | 700/284 |
| 2020/0359580 A1* | 11/2020 | Montgomery | ............... | A01G 25/02 |

* cited by examiner

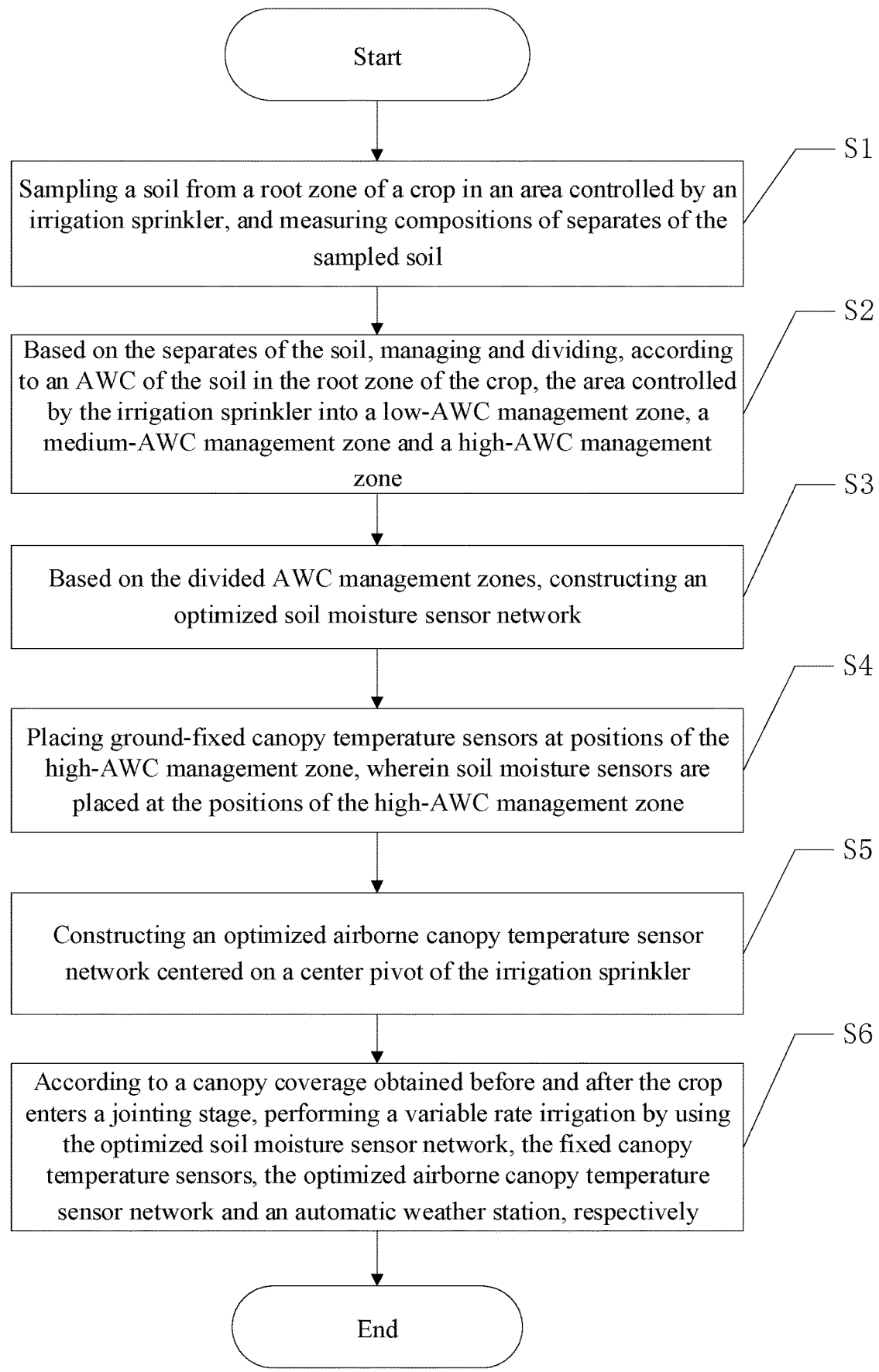

DECISION-MAKING METHOD FOR VARIABLE RATE IRRIGATION MANAGEMENT

CROSS REFERENCE TO THE RELATED APPLICATIONS

This application is based upon and claims priority to Chinese Patent Application No. 202110243593.4, filed on Mar. 5, 2021, the entire contents of which are incorporated herein by reference.

TECHNICAL FIELD

The present invention belongs to the technical field of agricultural information measurement and agricultural irrigation, and more particularly, relates to a decision-making method for variable rate irrigation management.

BACKGROUND

Compared with traditional uniform irrigation, variable rate irrigation systems are capable of spraying water at a variable rate simultaneously in both the travel direction and the truss direction of the irrigation sprinkler, and thus have potential advantages in improving the water management level and water use efficiency. At present, variable rate irrigation systems have been commercially available, but there is still a lack of scientific basic information and irrigation decision-making methods for precise spatial variable rate water management, which limits the popularization and application of variable rate irrigation technology. In order to fully exploit the advantages of variable rate irrigation technology, it is highly desirable to integrate complex sensor networks in a variable rate irrigation system and develop a decision-making method to sense changes in the field in real time and generate dynamic prescription maps for variable rate irrigation.

SUMMARY

To solve the problems in the real-time dynamic and precise management of variable rate irrigation technology, an objective of the present invention is to provide a decision-making method for variable rate irrigation management.

The technical solutions of the present invention are as follows. A decision-making method for variable rate irrigation management includes the following steps:

S1: sampling a soil from a root zone of a crop in an area controlled by an irrigation sprinkler, and measuring compositions of separates of the sampled soil;

S2: based on the separates of the soil, managing and dividing, according to an available water capacity (AWC) of the soil in the root zone of the crop, the area controlled by the irrigation sprinkler into a low-AWC management zone, a medium-AWC management zone and a high-AWC management zone;

S3: based on the divided AWC management zones, constructing an optimized soil moisture sensor network;

S4: placing ground-fixed canopy temperature sensors at positions of the high-AWC management zone, wherein soil moisture sensors are placed at the positions of the high-AWC management zone;

S5: constructing an optimized airborne canopy temperature sensor network centered on a center pivot of the irrigation sprinkler; and S6: according to a canopy coverage obtained before and after the crop enters a jointing stage, performing a variable rate irrigation by using the optimized soil moisture sensor network, the fixed canopy temperature sensors, the optimized airborne canopy temperature sensor network and an automatic weather station, respectively.

Further, in step S1, a method for sampling and measuring the soil includes: sampling by using a square grid method, and measuring the compositions of the separates of the soil with a root dry weight distribution of $\geq 80\%$ by depths in the root zone of the crop in the area controlled by the irrigation sprinkler, wherein the separates of the soil include sand particles, silt particles and clay particles, and the number of square grids is greater than or equal to 100.

Further, in step S2, a method for managing and dividing the area controlled by the irrigation sprinkler includes: based on the separates of the soil, calculating the AWC of the soil in the root zone of the crop by using Rosetta software, and performing management and division on the AWC of the soil in the root zone of the crop by using a Jenks natural breaks classification method to obtain the low-AWC management zone, the medium-AWC management zone and the high-AWC management zone.

Further, step S3 includes the following sub-steps:

S31: calculating an average clay content $\overline{Clay}$ in each AWC management zone; and S32: for each AWC management zone, placing the soil moisture sensors at the positions each with 1.1-1.2 times the average clay content $\overline{Clay}$ to construct the optimized soil moisture sensor network.

Further, in step S31, the average clay content $\overline{Clay}$ is calculated according to the following formula:

$$\overline{Clay} = \sum_{i=1}^{n} Clay_i;$$

wherein, n represents the number of grids contained in each AWC management zone for measuring the compositions of the separates of the soil, and $Clay_i$ represents an average clay content of a soil in a root zone of a crop in an $i^{th}$ grid.

Further, step S5 includes the following sub-steps:

S51: discretely creating concentric circles with different radii centered on the center pivot of the irrigation sprinkler;

S52: when the number of the concentric circles with circumferences intersecting with the square grids is greater than or equal to 100, taking the number of the concentric circles as the minimum number of airborne canopy temperature sensors placed along the truss direction of the irrigation sprinkler; and S53: according to the minimum number of the airborne canopy temperature sensors, constructing the optimized airborne canopy temperature sensor network.

Further, in step S53, a method for constructing the optimized airborne canopy temperature sensor network includes: according to distances between the airborne canopy temperature sensors and the center pivot of the irrigation sprinkler, based on a principle that measurement data obtained from each airborne canopy temperature sensor represents an equal observation area, optimizing positions of the airborne canopy temperature sensors placed along the truss direction of the irrigation sprinkler; and calculating a distance $R_m$ between an $m^{th}$ airborne canopy temperature sensor and the center pivot of the irrigation sprinkler according to the following formula:

$$R_m = R \times \sqrt{m}/\sqrt{X};$$

wherein, R represents the radius of a circular area irrigated by the center pivot irrigation sprinkler, and X represents the number of sensors.

Further, in step S6, if the crop has not entered the jointing stage, a method for monitoring soil moisture content data by using the optimized soil moisture sensor network and performing the variable rate irrigation specifically includes: performing the irrigation when a soil moisture content in any AWC management zone reaches a set irrigation water lower limit, wherein a water amount for the variable rate irrigation is determined by a difference between an irrigation water upper limit and a measured soil moisture content in each AWC management zone; and if the crop has entered the jointing stage, performing the irrigation when the soil moisture content in any AWC management zone reaches the set irrigation water lower limit; under semi-arid climate conditions, performing the variable rate irrigation by using the fixed canopy temperature sensors, the optimized airborne canopy temperature sensor network and monitoring data obtained from the weather station; and under semi-humid climate conditions, performing the variable rate irrigation by using the optimized soil moisture sensor network, the optimized airborne canopy temperature sensor network and the fixed canopy temperature sensors.

Further, in step S6, if the crop has entered the jointing stage, a method for performing the variable rate irrigation by using the fixed canopy temperature sensors, the optimized airborne canopy temperature sensor network and the monitoring data obtained from the weather station under the semi-arid climate conditions includes:

A61: when the soil moisture content in any AWC management zone reaches the set irrigation water lower limit, operating the irrigation sprinkler for one rotation at a 100% speed to obtain scattered point values of a canopy temperature of the entire field;

A62: determining a sampling time interval of the canopy temperature according to a requirement of the number of the scattered point values of the canopy temperature;

A63: based on the sampling time interval of the canopy temperature, taking the canopy temperature of a fixed point as a reference, and converting, by using a time scale conversion method, the scattered point values of the canopy temperature into canopy temperatures at the time when a daily maximum canopy temperature occurs;

A64: calculating a normalized relative canopy temperature NRCT based on the canopy temperatures obtained after the time scale conversion;

A65: according to the normalized relative canopy temperature NRCT generating an NRCT spatial distribution map by using an ordinary Kriging interpolation;

A66: dividing the entire field into a low-water deficit dynamic management zone, a medium-water deficit dynamic management zone and a high-water deficit dynamic management zone according to different ranges of the NRCT spatial distribution map; and A67: calculating an irrigation water quota $I_1$ in each water deficit dynamic management zone based on the normalized relative canopy temperature NRCT and a water requirement $ET_c$ of the crop in an interval between two irrigation times, and creating a prescription map for the variable rate irrigation.

In step S6, if the crop has entered the jointing stage, a method for performing the variable rate irrigation by using the optimized soil moisture sensor network, the optimized airborne canopy temperature sensor network and the fixed canopy temperature sensors under the semi-humid climate conditions includes:

B61: when the soil moisture content in any AWC management zone reaches the set irrigation water lower limit, operating the irrigation sprinkler for one rotation at the 100% speed to obtain the scattered point values of the canopy temperature of the entire field;

B62: determining the sampling time interval of the canopy temperature according to the requirement of the number of the scattered point values of the canopy temperature;

B63: based on the sampling time interval of the canopy temperature, taking the canopy temperature of the fixed point as the reference, and converting, by using the time scale conversion method, the scattered point values of the canopy temperature into the canopy temperatures at the time when the daily maximum canopy temperature occurs;

B64: calculating the normalized relative canopy temperature NRCT based on the canopy temperatures obtained after the time scale conversion;

B65: according to the normalized relative canopy temperature NRCT, generating the NRCT spatial distribution map by using the ordinary Kriging interpolation;

B66: dividing the entire field into the low-water deficit dynamic management zone, the medium-water deficit dynamic management zone and the high-water deficit dynamic management zone according to the different ranges of the NRCT spatial distribution map;

B67: setting a preliminary irrigation water quota I';

B68: calculating a corrected irrigation water amount $I_m$ based on the irrigation water quota I' and rainfall forecast information;

B69: calculating an irrigation water quota $I_2$ in each water deficit dynamic management zone based on the normalized relative canopy temperature NRCT and the corrected irrigation water amount $I_m$, and creating the prescription map for the variable rate irrigation.

Further, in both step A62 and step B62, a method for determining the sampling time interval of the canopy temperature includes: determining the sampling time interval of the canopy temperature based on a criterion that the number of the scattered point values is in the range of 162-572.

In both step A64 and step B64, the normalized relative canopy temperature NRCT is calculated according to the following formula:

$$NRCT = \frac{T - T_{min}}{T_{max} - T_{min}};$$

wherein, T represents a canopy temperature of each measurement point in the field after the time scale conversion, $T_{max}$ represents the maximum canopy temperature of the field after the time scale conversion, and $T_{min}$ represents the minimum canopy temperature of the field after the time scale conversion.

In step A67, the water requirement $ET_c$ of the crop in the interval between the two irrigation times is calculated according to the following formula:

$$ET_c = K_c \times ET_0;$$

wherein, $$ET_0 = \frac{0.408\Delta(R_n - G) + \gamma \frac{900}{T+273} u_2(e_s - e_a)}{\Delta + \gamma(1 + 0.43u_2)},$$

$ET_0$ represents a reference evapotranspiration of the crop, $K_c$ represents a crop coefficient, $R_n$ represents a net radiation at the surface of the crop, G represents a soil heat flux density, $\gamma$ represents a psychrometric constant, T represents a mean daily air temperature at 2-meter height, and $u_2$ represents a wind speed at 2-meter height, $e_s$ represents a saturation vapor pressure, $e_a$ represents an actual vapor pressure, and $\Delta$ represents a slope of a saturation vapor pressure curve.

In step A67, the irrigation water quota $I_1$ in each water deficit dynamic management zone is calculated according to the following formula:

$$\begin{cases} I_1 = 100\%\ ET_c & 0.67 < NRCT \leq 1.0 \\ I_1 = 67\%\ ET_c & 0.33 < NRCT \leq 0.67. \\ I_1 = 33\%\ ET_c & 0 \leq NRCT \leq 0.33 \end{cases}$$

In step B68, the corrected irrigation water amount $I_m$ is calculated according to the following formula:

$$\begin{cases} I_m = 100\% \times I' & P < 10\ \text{mm} \\ I_m = 80\% \times I' & 10\ \text{mm} \leq P < 50\ \text{mm}; \\ I_m = 60\% \times I' & 50\ \text{mm} \leq P \end{cases}$$

wherein, P represents a rainfall amount from a weather forecast for the next 3 days, and I' represents the preliminary irrigation water quota.

In step B69, the irrigation water quota $I_2$ in each water deficit dynamic management zone is calculated according to the following formula:

$$\begin{cases} I_2 = 100\%\ I_m & 0.67 < NRCT \leq 1.0 \\ I_2 = 67\%\ I_m & 0.33 < NRCT \leq 0.67. \\ I_2 = 33\%\ I_m & 0 \leq NRCT \leq 0.33 \end{cases}$$

The advantages of the present invention are as follows. According to the present invention, on one hand, the decision-making method for variable rate irrigation management optimizes the placement and quantity of the soil moisture sensor network and the canopy temperature sensor network to improve the measurement accuracy while reducing the cost of the variable rate irrigation system. On the other hand, the decision-making method for variable rate irrigation management overcomes shortcomings in the prior art. Prior methods typically ignore the temporal and spatial changes in crop water deficit when relying solely on soil moisture sensors or meteorological parameters to calculate the irrigation water amount. The measurement accuracy is easily affected by factors such as insufficient canopy coverage in the early stage of crop growth and cloudy weather when the spatial distribution characteristics of crop water deficit are obtained solely by the canopy temperature sensors. Moreover, decisions about different prescription maps for variable rate irrigation are made according to different rainfall in the growth stage of the crop, which is conducive to improving the accuracy of water management.

BRIEF DESCRIPTION OF THE DRAWINGS

FIGURE is a flow chart of the decision-making method for variable rate irrigation management.

DETAILED DESCRIPTION OF THE EMBODIMENTS

Embodiments of the present invention will be further described below in conjunction with the drawings.

As shown in FIG. 1, the present invention provides a decision-making method for variable rate irrigation management, including the following steps:
S1: a soil is sampled from a root zone of a crop in an area controlled by an irrigation sprinkler, and compositions of separates of the sampled soil are measured;
S2: based on the separates of the soil, the area controlled by the irrigation sprinkler is managed and divided into a low-AWC management zone, a medium-AWC management zone and a high-AWC management zone according to an AWC of the soil in the root zone of the crop;
S3: based on the divided AWC management zones, an optimized soil moisture sensor network is constructed;
S4: ground-fixed canopy temperature sensors are placed at positions of the high-AWC management zone, wherein soil moisture sensors are placed at the positions of the high-AWC management zone;
S5: an optimized airborne canopy temperature sensor network centered on the center pivot of the irrigation sprinkler is constructed; and
S6: according to a canopy coverage obtained before and after the crop enters a jointing stage, a variable rate irrigation is performed by using the optimized soil moisture sensor network, the fixed canopy temperature sensors, the optimized airborne canopy temperature sensor network and an automatic weather station, respectively.

In an embodiment of the present invention, as shown in FIG. 1, in step S1, a method for sampling and measuring the soil includes: sampling by using a square grid method, and measuring the compositions of the separates of the soil with a root dry weight distribution of $\geq 80\%$ by depths in the root zone of the crop in the area controlled by the irrigation sprinkler, wherein the separates of the soil include sand particles, silt particles and clay particles, and the number of sampling points is not less than 100 in order to meet the requirements of interpolation accuracy.

In an embodiment of the present invention, as shown in FIG. 1, in step S1, a method for sampling and measuring the soil includes: sampling by using a square grid method, and measuring the compositions of the separates of the soil with a root dry weight distribution of $\geq 80\%$ by depths in the root zone of the crop in the area controlled by the irrigation sprinkler, wherein the separates of the soil include sand particles, silt particles and clay particles, and the number of square grids is greater than or equal to 100.

In an embodiment of the present invention, as shown in FIG. 1, step S3 includes the following sub-steps:
S31: an average clay content $\overline{Clay}$ in each AWC management zone is calculated; and S32: for each AWC management zone, the soil moisture sensors are placed at the positions each with 1.1-1.2 times the average clay content $\overline{\text{Clay}}$ to construct the optimized soil moisture sensor network.

In an embodiment of the present invention, as shown in FIG. 1, in step S31, the average clay content $\overline{\text{Clay}}$ is calculated according to the following formula:

$$\overline{\text{Clay}} = \sum_{i=1}^{n} \text{Clay}_i;$$

wherein, n represents the number of grids contained in each AWC management zone for measuring the compositions of the separates of the soil, and $\text{Clay}_i$ represents an average clay content of a soil in a root zone of a crop in the $i^{th}$ grid.

In an embodiment of the present invention, as shown in FIG. 1, step S5 includes the following sub-steps:
- S51: concentric circles with different radii centered on the center pivot of the irrigation sprinkler are discretely created;
- S52: when the number of the concentric circles with circumferences intersecting with the square grids is greater than or equal to 100, the number of the concentric circles is taken as the minimum number of the airborne canopy temperature sensors placed along the truss direction of the irrigation sprinkler; and
- S53: according to the minimum number of the airborne canopy temperature sensors, the optimized airborne canopy temperature sensor network is constructed.

In an embodiment of the present invention, as shown in FIG. 1, in step S53, a method for constructing the optimized airborne canopy temperature sensor network includes: according to distances between the airborne canopy temperature sensors and the center pivot of the irrigation sprinkler, based on a principle that measurement data obtained from each airborne canopy temperature sensor represents an equal observation area, optimizing the positions of the airborne canopy temperature sensors placed along the truss direction of the irrigation sprinkler; and calculating the distance $R_m$ between the $m^{th}$ airborne canopy temperature sensor and the center pivot of the irrigation sprinkler according to the following formula:

$$R_m = R \times \sqrt{m}/\sqrt{X};$$

wherein, R represents the radius of a circular area irrigated by the center pivot irrigation sprinkler, and X represents the number of sensors.

In an embodiment of the present invention, as shown in FIG. 1, in step S6, if the crop has not entered the jointing stage, a method for monitoring soil moisture content data by using the optimized soil moisture sensor network and performing the variable rate irrigation specifically includes: performing the irrigation when a soil moisture content in any AWC management zone reaches a set irrigation water lower limit, wherein a water amount for the variable rate irrigation is determined by a difference between an irrigation water upper limit and a measured soil moisture content in each AWC management zone; and if the crop has entered the jointing stage, performing the irrigation when the soil moisture content in any AWC management zone reaches the set irrigation water lower limit; under semi-arid climate conditions, performing the variable rate irrigation by using the fixed canopy temperature sensors, the optimized airborne canopy temperature sensor network and monitoring data obtained from the weather station; and under semi-humid climate conditions, performing the variable rate irrigation by using the optimized soil moisture sensor network, the optimized airborne canopy temperature sensor network and the fixed canopy temperature sensors.

In an embodiment of the present invention, as shown in FIG. 1, in step S6, if the crop has entered the jointing stage, a method for performing the variable rate irrigation by using the fixed canopy temperature sensors, the optimized airborne canopy temperature sensor network and the monitoring data obtained from the weather station under the semi-arid climate conditions includes:
- A61: when the soil moisture content in any AWC management zone reaches the set irrigation water lower limit, the irrigation sprinkler is operated for one rotation at the 100% speed to obtain scattered point values of a canopy temperature of the entire field;
- A62: a sampling time interval of the canopy temperature is determined according to a requirement of the number of the scattered point values of the canopy temperature;
- A63: based on the sampling time interval of the canopy temperature, the canopy temperature of a fixed point is taken as a reference, and the scattered point values of the canopy temperature are converted by using a time scale conversion method into canopy temperatures at the time when a daily maximum canopy temperature occurs;
- A64: a normalized relative canopy temperature NRCT is calculated based on the canopy temperatures obtained after the time scale conversion;
- A65: according to the normalized relative canopy temperature NRCT, an NRCT spatial distribution map is generated by using an ordinary Kriging interpolation;
- A66: the entire field is divided into a low-water deficit dynamic management zone, a medium-water deficit dynamic management zone and a high-water deficit dynamic management zone according to different ranges of the NRCT spatial distribution map; and
- A67: an irrigation water quota $I_1$ in each water deficit dynamic management zone is calculated based on the normalized relative canopy temperature NRCT and a water requirement $ET_c$ of the crop in an interval between two irrigation times, and a prescription map for the variable rate irrigation is created.

In step S6, if the crop has entered the jointing stage, a method for performing the variable rate irrigation by using the optimized soil moisture sensor network, the optimized airborne canopy temperature sensor network and the fixed canopy temperature sensors under the semi-humid climate conditions includes:
- B61: when the soil moisture content in any AWC management zone reaches the set irrigation water lower limit, the irrigation sprinkler is operated for one rotation at the 100% speed to obtain the scattered point values of the canopy temperature of the entire field;
- B62: the sampling time interval of the canopy temperature is determined according to the requirement of the number of the scattered point values of the canopy temperature;
- B63: based on the sampling time interval of the canopy temperature, the canopy temperature of the fixed point is taken as the reference, and the scattered point values of the canopy temperature are converted by using the time scale conversion method into the canopy temperatures at the time when the daily maximum canopy temperature occurs;

B64: the normalized relative canopy temperature NRCT is calculated based on the canopy temperatures obtained after the time scale conversion;

B65: according to the normalized relative canopy temperature NRCT, the NRCT spatial distribution map is generated by using the ordinary Kriging interpolation;

B66: the entire field is divided into the low-water deficit dynamic management zone, the medium-water deficit dynamic management zone and the high-water deficit dynamic management zone according to the different ranges of the NRCT spatial distribution map;

B67: a preliminary irrigation water quota I' is set;

B68: a corrected irrigation water amount $I_m$ is calculated based on the irrigation water quota I' and rainfall forecast information;

B69: an irrigation water quota $I_2$ in each water deficit dynamic management zone is calculated based on the normalized relative canopy temperature NRCT and the corrected irrigation water amount $I_m$, and the prescription map for the variable rate irrigation is created.

In an embodiment of the present invention, as shown in FIG. 1, in both step A62 and step B62, a method for determining the sampling time interval of the canopy temperature includes: determining the sampling time interval of the canopy temperature based on a criterion that the number of the scattered point values is in the range of 162-572.

In both step A64 and step B64, the normalized relative canopy temperature NRCT is calculated according to the following formula:

$$NRCT = \frac{T - T_{min}}{T_{max} - T_{min}};$$

wherein, T represents a canopy temperature of each measurement point in the field after the time scale conversion, $T_{max}$ represents the maximum canopy temperature of the field after the time scale conversion, and $T_{min}$ represents the minimum canopy temperature of the field after the time scale conversion.

In step A64, $$T_{rmt} = T_e + \frac{(T_{rmt,t} - T_e)(T_{ref} - T_e)}{(T_{ref,t} - T_e)},$$

wherein $T_{rmt}$ represents a predicted temperature value at any point excluding a reference point in the field at any time, and $T_e$ represents the minimum canopy temperature before dawn; $T_{rmt,1}$ represents a measured temperature of a non-reference point when the irrigation sprinkler passes the non-reference point at any time t during the day; $T_{ref}$ represents a measured temperature of the reference point at a required predicted time point, and $T_{ref,t}$ represents a measured temperature of the reference point when the irrigation sprinkler passes the non-reference point at any time t during the day.

In step A67, the water requirement $ET_c$ of the crop in the interval between the two irrigation times is calculated according to the following formula:

$$ET_c = K_c \times ET_0;$$

wherein, $$ET_0 = \frac{0.408\Delta(R_n - G) + \gamma \frac{900}{T + 273} u_2(e_s - e_a)}{\Delta + \gamma(1 + 0.43u_2)},$$

$ET_0$ represents a reference evapotranspiration of the crop, $K_c$ represents a crop coefficient, $R_n$ represents a net radiation at the surface of the crop, G represents a soil heat flux density, $\gamma$ represents a psychrometric constant, T represents a mean daily air temperature at 2-meter height, and $u_2$ represents a wind speed at 2-meter height, $e_s$ represents a saturation vapor pressure, $e_a$ represents an actual vapor pressure, and $\Delta$ represents a slope of a saturation vapor pressure curve.

In step A67, the irrigation water quota $I_1$ in each water deficit dynamic management zone is calculated according to the following formula:

$$\begin{cases} I_1 = 100\% \ ET_c & 0.67 < NRCT \le 1.0 \\ I_1 = 67\% \ ET_c & 0.33 < NRCT \le 0.67 \\ I_1 = 33\% \ ET_c & 0 \le NRCT \le 0.33 \end{cases}.$$

In step B68, the corrected irrigation water amount $I_m$ is calculated according to the following formula:

$$\begin{cases} I_m = 100\% \times I' & P < 10 \text{ mm} \\ I_m = 80\% \times I' & 10 \text{ mm} \le P < 50 \text{ mm} \\ I_m = 60\% \times I' & 50 \text{ mm} \le P \end{cases};$$

wherein, P represents a rainfall amount from a weather forecast for the next 3 days, and I' represents the preliminary irrigation water quota.

In step B69, the irrigation water quota $I_2$ in each water deficit dynamic management zone is calculated according to the following formula:

$$\begin{cases} I_2 = 100\% \ I_m & 0.67 < NRCT \le 1.0 \\ I_2 = 67\% \ I_m & 0.33 < NRCT \le 0.67 \\ I_2 = 33\% \ I_m & 0 \le NRCT \le 0.33 \end{cases}.$$

In an embodiment of the present invention, under semi-arid climate conditions, the water consumed by the crop is mainly provided by irrigation. Before the crop enters the jointing stage, due to an insufficient canopy coverage, the irrigation schedule is formulated based on the monitoring data obtained from the soil moisture sensor network. The irrigation is performed when the soil water capacity in any static management zone reaches the set irrigation water lower limit. The water amount for the variable rate irrigation is calculated based on the difference between the irrigation water upper limit and the measured soil water capacity in each management zone. After the crop enters the jointing stage, prescription maps for the variable rate irrigation are jointly formulated based on the monitoring data obtained from the canopy temperature sensors and the weather station. Under semi-arid climate conditions, there are fewer rainfall events and a higher irrigation frequency. In this regard, the irrigation time is determined according to a fixed irrigation interval to facilitate user management. For example, the irrigation interval of winter wheat in North China is taken as 10 days according to the test results. Within 1-2 days approaching the irrigation date, in a sunny and cloudless weather, the irrigation sprinkler is operated for one rotation at the 100% speed to obtain the scattered point values of the canopy temperature of the entire field. Based on a geographic information system (GIS) software, the normalized relative canopy temperature (NRCT) spatial distribution map of the water deficit index is generated for subsequent management and division. The irrigation water quota in each management zone is equal to the product of an average NRCT and $ET_c$ in the interval between two irrigation times, wherein $ET_c$ is calculated by using meteorological parameters and the Penman-Monteith (P-M) equation.

Under semi-humid climate conditions, the water consumed by the crop is mainly provided by rainfall and irrigation. Before the crop enters the jointing stage, due to an insufficient canopy coverage, the irrigation schedule is formulated based on the monitoring data obtained from the soil moisture sensor network. The irrigation is performed when the soil water capacity in any static management zone reaches the set irrigation water lower limit. The water amount for the variable rate irrigation is calculated based on the difference between the irrigation water upper limit and the measured soil water capacity in each management zone. After the crop enters the jointing stage, it is difficult to accurately estimate the amount of water consumed by the crop due to a high frequency of rainfall events, and the prescription maps for the variable rate irrigation are jointly formulated based on the monitoring data obtained from the soil moisture sensors and the canopy temperature sensors. When the soil water capacity in any static management zone is close to the irrigation water lower limit, in a sunny and cloudless weather, the irrigation sprinkler is operated for one rotation at the 100% speed to obtain the scattered point values of the canopy temperature of the entire field. Based on the GIS software, the NRCT spatial distribution map is generated for subsequent management and division. Considering that a rainfall event may occur after the irrigation, the irrigation water quota is preliminarily designed to be a fixed value of 20 mm, and will be corrected based on the rainfall forecast information for the next 3 days. The irrigation water quota in each management zone is equal to the product of the corrected irrigation depth and the average NRCT.

The working principle and process of the present invention are as follows. The present invention proposes a method integrating parameter acquisition of soil, plant, and atmospheric information with irrigation decision-making, that is, a decision-making method for variable rate management using a center pivot irrigation sprinkler based on the coupling effects of multiple types of sensors. The method specifically includes: optimizing and screening the placement of the soil moisture sensor network; optimizing the placement and quantity of the canopy temperature sensor network along the truss direction of the irrigation sprinkler; determining the irrigation time for semi-arid and semi-humid climate conditions by integrating the coupling effects of multiple types of sensors; and generating prescription maps for the variable rate irrigation.

The advantages of the present invention are as follows. According to the present invention, on one hand, the decision-making method for variable rate irrigation management optimizes the placement and quantity of the soil moisture sensor network and the canopy temperature sensor network to improve the measurement accuracy while reducing the cost of the variable rate irrigation system. On the other hand, the decision-making method for variable rate irrigation management overcomes shortcomings in the prior art. Prior methods typically ignore the temporal and spatial changes in crop water deficit when relying solely on soil moisture sensors or meteorological parameters to calculate the irrigation water amount. The measurement accuracy is easily affected by factors such as insufficient canopy coverage in the early stage of crop growth and cloudy weather when the spatial distribution characteristics of crop water deficit are obtained solely by the canopy temperature sensors. Moreover, decisions about different prescription maps for variable rate irrigation are made according to different rainfall in the growth stage of the crop, which is conducive to improving the accuracy of water management.

Those of ordinary skill in the art shall realize that the embodiments described herein are used to help readers understand the principles of the present invention. It should be understood that the scope of protection of the present invention is not limited to such specific descriptions and embodiments. Those of ordinary skill in the art can make various modifications and combinations without departing from the essence of the present invention based on the technical teachings disclosed in the present invention, and these modifications and combinations shall fall within the scope of protection of the present invention.

What is claimed is:

1. A decision-making method for a variable rate irrigation management, comprising the following steps:

S1: sampling a soil from a root zone of a crop in an area controlled by an irrigation sprinkler, and measuring compositions of separates of the soil;

S2: based on the separates of the soil, managing and dividing, according to an available water capacity (AWC) of the soil in the root zone of the crop, the area controlled by the irrigation sprinkler into a low-AWC management zone, a medium-AWC management zone and a high-AWC management zone;

S3: based on the low-AWC management zone, the medium-AWC management zone and the high-AWC management zone, constructing an optimized soil moisture sensor network;

S4: placing ground-fixed canopy temperature sensors at positions of the high-AWC management zone, wherein soil moisture sensors are placed at the positions of the high-AWC management zone;

S5: constructing an optimized airborne canopy temperature sensor network centered on a center pivot of the irrigation sprinkler; and S6: according to a canopy coverage obtained before and after the crop enters a jointing stage, performing a variable rate irrigation by using the optimized soil moisture sensor network, the ground-fixed canopy temperature sensors, the optimized airborne canopy temperature sensor network and an automatic weather station, respectively, wherein in step S2, the managing and dividing of the area controlled by the irrigation sprinkler comprises:

based on the separates of the soil, calculating the AWC of the soil in the root zone of the crop by using a Rosetta software, and performing a management and division on the AWC of the soil in the root zone of the crop by using a Jenks natural breaks classification method to obtain the low-AWC management zone, the medium-AWC management zone, and the high-AWC management zone.

2. The decision-making method according to claim 1, wherein in step S1, a method for sampling and measuring the soil comprises:

sampling by using a square grid method, and measuring the compositions of the separates of the soil with a root dry weight distribution of ≥80% by depths in the root zone of the crop in the area controlled by the irrigation sprinkler, wherein the separates of the soil comprise sand particles, silt particles and clay particles, and a number of square grids is greater than or equal to 100.

3. The decision-making method according to claim 1, wherein
step S3 comprises the following sub-steps:
S31: calculating an average clay content $\overline{\text{Clay}}$ in each of the low-AWC management zone, the medium-AWC management zone and the high-AWC management zone; and
S32: for each of the low-AWC management zone, the medium-AWC management zone and the high-AWC management zone, placing the soil moisture sensors at the positions each with 1.1-1.2 times the average clay content $\overline{\text{Clay}}$ to construct the optimized soil moisture sensor network.

4. The decision-making method according to claim 3, wherein
in step S31, the average clay content $\overline{\text{Clay}}$ is calculated according to the following formula:

$$\overline{\text{Clay}} = \sum_{i=1}^{n} \text{Clay}_i;$$

wherein, n represents a number of grids contained in each of the low-AWC management zone, the medium-AWC management zone and the high-AWC management zone for measuring the compositions of the separates of the soil, and $\text{Clay}_i$ represents an average clay content of a soil in a root zone of a crop in an ith grid.

5. The decision-making method according to claim 1, wherein
step S5 comprises the following sub-steps:
S51: discretely creating concentric circles with different radii centered on the center pivot of the irrigation sprinkler;
S52: when a number of the concentric circles with circumferences intersecting with square grids is greater than or equal to 100, taking the number of the concentric circles as a minimum number of airborne canopy temperature sensors placed along a truss direction of the irrigation sprinkler; and
S53: according to the minimum number of the airborne canopy temperature sensors, constructing the optimized airborne canopy temperature sensor network.

6. The decision-making method according to claim 5, wherein
in step S53, a method for constructing the optimized airborne canopy temperature sensor network comprises:
according to distances between the airborne canopy temperature sensors and the center pivot of the irrigation sprinkler, based on a principle that measurement data obtained from each of the airborne canopy temperature sensors represents an equal observation area, optimizing positions of the airborne canopy temperature sensors placed along the truss direction of the irrigation sprinkler; and
calculating a distance $R_m$ between an mth airborne canopy temperature sensor of the airborne canopy temperature sensors and the center pivot of the irrigation sprinkler according to the following formula:

$R_m = R \times \sqrt{m}/\sqrt{X};$ wherein, R represents a radius of a circular area irrigated by the center pivot irrigation sprinkler, and X represents a number of the airborne canopy temperature sensors.

7. The decision-making method according to claim 1, wherein
in step S6, if the crop has not entered the jointing stage, a method for monitoring soil moisture content data by using the optimized soil moisture sensor network and performing the variable rate irrigation specifically comprises:
performing the variable rate irrigation when a soil moisture content in one of the low-AWC management zone, the medium-AWC management zone and the high-AWC management zone reaches a set irrigation water lower limit, wherein a water amount for the variable rate irrigation is determined by a difference between an irrigation water upper limit and a measured soil moisture content in each of the low-AWC management zone, the medium-AWC management zone and the high-AWC management zone; and
if the crop has entered the jointing stage, performing the variable rate irrigation when the soil moisture content in one of the low-AWC management zone, the medium-AWC management zone and the high-AWC management zone reaches the set irrigation water lower limit; under semi-arid climate conditions, performing the variable rate irrigation by using the ground-fixed canopy temperature sensors, the optimized airborne canopy temperature sensor network and monitoring data obtained from the automatic weather station; and under semi-humid climate conditions, performing the variable rate irrigation by using the optimized soil moisture sensor network, the optimized airborne canopy temperature sensor network and the ground-fixed canopy temperature sensors.

8. The decision-making method according to claim 7, wherein
in step S6, if the crop has entered the jointing stage, a method for performing the variable rate irrigation by using the ground-fixed canopy temperature sensors, the optimized airborne canopy temperature sensor network and the monitoring data obtained from the automatic weather station under the semi-arid climate conditions comprises:
A61: when the soil moisture content in one of the low-AWC management zone, the medium-AWC management zone and the high-AWC management zone reaches the set irrigation water lower limit, operating the irrigation sprinkler for a rotation at a 100% speed to obtain scattered point values of a canopy temperature of a field;
A62: determining a sampling time interval of the canopy temperature according to a requirement of a number of the scattered point values of the canopy temperature;
A63: based on the sampling time interval of the canopy temperature, taking the canopy temperature of a fixed point as a reference, and converting, by using a time scale conversion method, the scattered point values of the canopy temperature into canopy temperatures at a time when a daily maximum canopy temperature occurs;
A64: calculating a normalized relative canopy temperature NRCT based on the canopy temperatures obtained at the time when the daily maximum canopy temperature occurs after a time scale conversion;

A65: according to the normalized relative canopy temperature NRCT, generating an NRCT spatial distribution map by using an ordinary Kriging interpolation;

A66: dividing the field into a low-water deficit dynamic management zone, a medium-water deficit dynamic management zone and a high-water deficit dynamic management zone according to different ranges of the NRCT spatial distribution map; and A67: calculating an irrigation water quota $I_1$ in in each of the low-water deficit dynamic management zone, the medium-water deficit dynamic management zone and the high-water deficit dynamic management zone based on the normalized relative canopy temperature NRCT and a water requirement $ET_c$ of the crop in an interval between two irrigation times, and creating a prescription map for the variable rate irrigation; wherein in step S6, if the crop has entered the jointing stage, a method for performing the variable rate irrigation by using the optimized soil moisture sensor network, the optimized airborne canopy temperature sensor network and the ground-fixed canopy temperature sensors under the semi-humid climate conditions comprises:

B61: when the soil moisture content in one of the low-AWC management zone, the medium-AWC management zone and the high-AWC management zone reaches the set irrigation water lower limit, operating the irrigation sprinkler for the rotation at the 100% speed to obtain the scattered point values of the canopy temperature of the field;

B62: determining the sampling time interval of the canopy temperature according to the requirement of the number of the scattered point values of the canopy temperature;

B63: based on the sampling time interval of the canopy temperature, taking the canopy temperature of the fixed point as the reference, and converting, by using the time scale conversion method, the scattered point values of the canopy temperature into the canopy temperatures at the time when the daily maximum canopy temperature occurs;

B64: calculating the normalized relative canopy temperature NRCT based on the canopy temperatures obtained after the time scale conversion;

B65: according to the normalized relative canopy temperature NRCT, generating the NRCT spatial distribution map by using the ordinary Kriging interpolation;

B66: dividing the field into the low-water deficit dynamic management zone, the medium-water deficit dynamic management zone and the high-water deficit dynamic management zone according to the different ranges of the NRCT spatial distribution map;

B67: setting a preliminary irrigation water quota $I'$;

B68: calculating a corrected irrigation water amount $I_m$ based on the preliminary irrigation water quota $I'$ and rainfall forecast information;

B69: calculating an irrigation water quota $I_2$ in each of the low-water deficit dynamic management zone, the medium-water deficit dynamic management zone and the high-water deficit dynamic management zone based on the normalized relative canopy temperature NRCT and the corrected irrigation water amount $I_m$, and creating the prescription map for the variable rate irrigation.

9. The decision-making method according to claim 8, wherein in both step A62 and step B62, a method for determining the sampling time interval of the canopy temperature comprises:

determining the sampling time interval of the canopy temperature based on a criterion that the number of the scattered point values is in a range of 162-572;

in both step A64 and step B64, the normalized relative canopy temperature NRCT is calculated according to the following formula:

$$NRCT = \frac{T - T_{min}}{T_{max} - T_{min}};$$

wherein, T represents a canopy temperature of each measurement point in the field after the time scale conversion, $T_{max}$ represents a maximum canopy temperature of the field after the time scale conversion, and $T_{min}$ represents a minimum canopy temperature of the field after the time scale conversion;

in step A67, the water requirement $ET_c$ of the crop in the interval between the two irrigation times is calculated according to the following formula:

$$ET_c = K_c \times ET_0;$$

wherein, $$ET_0 = \frac{0.408\Delta(R_n - G) + \gamma \frac{900}{T + 273} u_2(e_s - e_a)}{\Delta + \gamma(1 + 0.43u_2)},$$

$ET_0$ represents a reference evapotranspiration of the crop, $D_c$ represents a crop coefficient, $R_n$ represents a net radiation at a surface of the crop, G represents a soil heat flux density, $\gamma$ represents a psychrometric constant, T represents a mean daily air temperature at a 2-meter height, and $u_2$ represents a wind speed at the 2-meter height, $e_s$ represents a saturation vapor pressure, $e_a$ represents an actual vapor pressure, and $\Delta$ represents a slope of a saturation vapor pressure curve;

in step A67, the irrigation water quota $I_1$ in each of the low-water deficit dynamic management zone, the medium-water deficit dynamic management zone and the high-water deficit dynamic management zone is calculated according to the following formula:

$$\begin{cases} I_1 = 100\% \ ET_c & 0.67 < NRCT \leq 1.0 \\ I_1 = 67\% \ ET_c & 0.33 < NRCT \leq 0.67 ; \\ I_1 = 33\% \ ET_c & 0 \leq NRCT \leq 0.33 \end{cases}$$

in step B68, the corrected irrigation water amount $I_m$ is calculated according to the following formula:

$$\begin{cases} I_m = 100\% \times I' & P < 10 \text{ mm} \\ I_m = 80\% \times I' & 10 \text{ mm} \leq P < 50 \text{ mm} ; \\ I_m = 60\% \times I' & 50 \text{ mm} \leq P \end{cases}$$

wherein, P represents a rainfall amount from a weather forecast for next 3 days, and $I'$ represents the preliminary irrigation water quota; and in step B69, the irrigation water quota $I_2$ in each of the low-water deficit dynamic management zone, the medium-water deficit dynamic management zone and the high-water deficit dynamic management zone is calculated according to the following formula:

$$\begin{cases} I_2 = 100\% \ I_m & 0.67 < NRCT \le 1.0 \\ I_2 = 67\% \ I_m & 0.33 < NRCT \le 0.67 \\ I_2 = 33\% \ I_m & 0 \le NRCT \le 0.33 \end{cases} \qquad 5$$

\* \* \* \* \*